(12) United States Patent
Tokarz et al.

(10) Patent No.: US 12,408,944 B2
(45) Date of Patent: Sep. 9, 2025

(54) CANNULA ASSEMBLY INCLUDING A SUCTION CUP SEAL

(71) Applicant: Covidien LP, Mansfield, MA (US)

(72) Inventors: Christopher A. Tokarz, Torrington, CT (US); Douglas M. Pattison, East Hartford, CT (US); Kevin M. Desjardin, Prospect, CT (US); Astley C. Lobo, West Haven, CT (US); Satish Gundala, Hyderabad (IN)

(73) Assignee: Covidien LP, Mansfield, MA (US)

( * ) Notice: Subject to any disclaimer, the term of this patent is extended or adjusted under 35 U.S.C. 154(b) by 454 days.

(21) Appl. No.: 17/145,677

(22) Filed: Jan. 11, 2021

(65) Prior Publication Data
US 2022/0218391 A1    Jul. 14, 2022

(51) Int. Cl.
*A61B 17/34* (2006.01)

(52) U.S. Cl.
CPC .. *A61B 17/3423* (2013.01); *A61B 2017/3419* (2013.01)

(58) Field of Classification Search
CPC .. A61B 17/3423; A61B 17/3417; A61B 17/34
See application file for complete search history.

(56) References Cited

U.S. PATENT DOCUMENTS

| | | | |
|---|---|---|---|
| 4,338,937 A * | 7/1982 | Lerman | A61F 2/0018 600/32 |
| 5,073,169 A | 12/1991 | Raiken | |
| 5,137,520 A | 8/1992 | Maxson et al. | |
| 5,176,648 A | 1/1993 | Holmes et al. | |
| 5,215,531 A * | 6/1993 | Maxson | A61M 25/02 128/DIG. 26 |
| 5,226,890 A | 7/1993 | Ianniruberto et al. | |
| 5,290,249 A | 3/1994 | Foster et al. | |
| 5,300,033 A | 4/1994 | Miller | |
| 5,330,497 A | 7/1994 | Freitas et al. | |
| 5,366,446 A | 11/1994 | Tal et al. | |
| 5,403,336 A | 4/1995 | Kieturakis et al. | |
| 5,484,420 A | 1/1996 | Russo | |
| 5,697,946 A | 12/1997 | Hopper et al. | |

(Continued)

FOREIGN PATENT DOCUMENTS

| | | | |
|---|---|---|---|
| CN | 201542606 U | * | 8/2010 |
| CN | 106236212 | | 12/2016 |

(Continued)

OTHER PUBLICATIONS

English Translation of CN-106236212-A (Year: 2016).*
Extended European Search Report dated May 17, 2022 issued in corresponding EP Appln. No. 22150864.1.

*Primary Examiner* — Darwin P Erezo
*Assistant Examiner* — Erin L Colello
(74) *Attorney, Agent, or Firm* — Draft Masters IP, LLC (57) ABSTRACT

A cannula assembly is utilized during a minimally invasive surgery to provide sealed access of a surgical instrument to an insufflated body cavity. The cannula assembly includes a cannula sleeve and a suction cup that is adjustably positionable on the cannula sleeve. The suction cup is formed of a compressible material such that when the suction cup is compressed or pressed against tissue by a clinician, the suction cup creates suction and engages tissue in a sealing relation.

18 Claims, 10 Drawing Sheets

(56) References Cited

U.S. PATENT DOCUMENTS

| | | | |
|---|---|---|---|
| 5,713,869 A | 2/1998 | Morejon | |
| 5,741,298 A * | 4/1998 | MacLeod | A61B 42/10 604/338 |
| 5,792,112 A | 8/1998 | Hart et al. | |
| 5,830,232 A | 11/1998 | Hasson | |
| 6,524,283 B1 | 2/2003 | Hopper et al. | |
| 6,589,211 B1 * | 7/2003 | MacLeod | A61B 17/3423 604/164.01 |
| 6,908,454 B2 | 6/2005 | McFarlane | |
| 7,235,064 B2 | 6/2007 | Hopper et al. | |
| 7,300,448 B2 | 11/2007 | Criscuolo et al. | |
| 7,316,699 B2 | 1/2008 | McFarlane | |
| 7,691,089 B2 * | 4/2010 | Gresham | A61B 17/3417 604/174 |
| 7,744,617 B2 | 6/2010 | Lunsford et al. | |
| 7,963,975 B2 | 6/2011 | Criscuolo | |
| 8,137,322 B2 | 3/2012 | Soltz et al. | |
| 8,147,453 B2 | 4/2012 | Albrecht et al. | |
| 8,162,893 B2 | 4/2012 | Okihisa et al. | |
| 8,262,568 B2 | 9/2012 | Albrecht et al. | |
| 8,287,503 B2 | 10/2012 | Albrecht et al. | |
| 8,382,707 B2 | 2/2013 | Albrecht et al. | |
| 8,430,851 B2 | 4/2013 | McGinley et al. | |
| 8,454,645 B2 | 6/2013 | Criscuolo et al. | |
| 8,480,575 B2 | 7/2013 | Albrecht et al. | |
| 8,597,250 B2 | 12/2013 | Okihisa et al. | |
| 8,721,537 B2 | 5/2014 | Albrecht et al. | |
| 8,795,161 B2 * | 8/2014 | Carter | A61B 17/0218 600/184 |
| 8,888,692 B1 * | 11/2014 | Pravongviengkham | B29C 49/08 600/207 |
| 8,894,571 B2 | 11/2014 | Albrecht et al. | |
| 8,939,946 B2 | 1/2015 | Albrecht et al. | |
| 9,259,238 B2 | 2/2016 | Albrecht et al. | |
| 9,522,265 B2 | 12/2016 | Pravong et al. | |
| 9,707,011 B2 * | 7/2017 | Malkowski | A61B 17/3423 |
| 10,064,649 B2 * | 9/2018 | Golebieski | A61B 17/3498 |
| 2003/0158572 A1 | 8/2003 | McFarlane | |
| 2004/0092796 A1 * | 5/2004 | Butler | A61B 17/3423 600/208 |
| 2004/0138702 A1 * | 7/2004 | Peartree | B25B 5/12 606/213 |
| 2004/0267096 A1 * | 12/2004 | Caldwell | A61B 90/40 600/213 |
| 2005/0113856 A1 | 5/2005 | Epstein et al. | |
| 2005/0165432 A1 | 7/2005 | Heinrich | |
| 2006/0079918 A1 | 4/2006 | Creston | |
| 2006/0106402 A1 * | 5/2006 | McLucas | A61B 17/3417 606/108 |
| 2007/0088277 A1 | 4/2007 | McGinley et al. | |
| 2009/0030443 A1 * | 1/2009 | Buser | A61B 17/3423 604/165.01 |
| 2009/0192467 A1 * | 7/2009 | Hansen | A61B 17/3462 604/174 |
| 2011/0054518 A1 * | 3/2011 | Carbunaru | A61B 17/3415 606/213 |
| 2013/0226288 A1 * | 8/2013 | Goldwasser | A61B 17/3421 623/2.1 |
| 2014/0257356 A1 | 9/2014 | Pacak et al. | |
| 2017/0056066 A1 | 3/2017 | Pravong et al. | |
| 2019/0053825 A1 * | 2/2019 | Ochoa | A61B 17/3421 |
| 2019/0307331 A1 * | 10/2019 | Saadat | A61B 34/20 |
| 2020/0323556 A1 | 10/2020 | George et al. | |

FOREIGN PATENT DOCUMENTS

| | | |
|---|---|---|
| CN | 106236212 A * | 12/2016 |
| EP | 0537768 | 4/1993 |
| EP | 0589452 A1 | 3/1994 |

* cited by examiner

CANNULA ASSEMBLY INCLUDING A SUCTION CUP SEAL

FIELD

The disclosure relates generally to surgical instruments, and more particularly, to a cannula assembly having a suction cup seal.

BACKGROUND

In order to facilitate minimally invasive surgery, a working space must be created in the desired surgical space. An insufflation gas, typically $CO_2$, is introduced into the abdomen of the patient to create an inflated state called pneumoperitoneum. Cannula assemblies are utilized to allow the introduction of surgical instrumentation and endoscopes (or other visualization tools). These cannula assemblies maintain the pressure of the pneumoperitoneum, as they have one or more seals. Typically, a "zero-seal" in the cannula assemblies seals a cannula assembly in the absence of a surgical instrument therein, and an instrument seal seals around a surgical instrument that is inserted through the cannula assembly. Further, these cannula assemblies may include, e.g., a foam, collar configured to secure the cannula assemblies in position.

In surgical procedures, it is desirable to adjust or manipulate surgical instrumentation extending through the cannula assemblies without compromising pneumoperitoneum. Therefore, it would be beneficial to have a cannula assembly with improved seal capability.

SUMMARY

In accordance with the disclosure, a cannula assembly includes a cannula housing, a cannula sleeve extending distally from the cannula housing, and a suction cup assembly adjustably securable over the cannula sleeve. The suction cup assembly includes a sealing component and a locking component. The sealing component includes a neck portion and inner and outer cups extending distally from the neck portion. The inner cup is nested within the outer cup. The sealing component is formed of a compressible material to create suction when pressed against tissue to form fluid-tight seals against tissue. The locking component is disposed about the neck portion of the sealing component. The locking component includes a locking sleeve and a latch coupled to the locking sleeve to selectively compress the locking sleeve to adjustably secure the suction cup assembly at a position along the cannula sleeve.

In an aspect, the cannula sleeve may have an inflatable balloon disposed at a distal end portion of the cannula sleeve.

In another aspect, the cannula housing may include an inflation port in communication with the inflatable balloon.

In yet another aspect, the inner cup may include an engaging portion defining an acute angle with respect to a longitudinal axis defined by the cannula sleeve when the inner cup is in an uncompressed state.

In still yet another aspect, the engaging portion of the inner cup may include a planar surface configured for planar contact with tissue in a sealing relation when the inner cup is compressed against tissue.

In still yet another aspect, the outer cup of the sealing component may include a first portion extending from the neck portion and a second portion deflected distally from the first portion.

In an aspect, the second portion of the outer cup may include a planar surface configured to be in a planar contact with tissue when compressed against tissue in a sealing relation.

In another aspect, the second portion of the outer cup may be distal of the inner cup.

In yet another aspect, at least the inner cup or the outer cup may be formed of a thermoplastic elastomer.

In still yet another aspect, the sealing component of the suction cup assembly may be monolithically formed.

In an aspect, the locking sleeve may define a slit to enable enlarging of the diameter of the locking sleeve by the latch.

In another aspect, the second portion of the outer cup may be disposed radially outwards of the inner cup when the suction cup assembly is compressed against tissue.

In yet another aspect, the locking sleeve may have a flange at a distal portion thereof. The flange may be configured to engage the outer cup of the sealing component to urge the outer cup radially outwards when the suction cup assembly is compressed against tissue.

In accordance with another aspect of the disclosure, a cannula assembly includes a cannula housing including an inflation port, a cannula sleeve extending from the cannula housing, and a suction cup adjustably disposed over the cannula sleeve. The cannula housing and the cannula sleeve define a lumen configured to receive a surgical instrument therethrough. The suction cup has a dome shape. The suction cup is compressible to form suction, thereby forming a seal against tissue.

In an aspect, the suction cup may be formed of a thermoplastic elastomer.

In another aspect, the suction cup may define a proximal aperture dimensioned to receive the cannula sleeve in a sealing relation.

In yet another aspect, the suction cup may further define a distal aperture having a diameter larger than a diameter of the proximal aperture.

In still yet another aspect, the suction cup may be frictionally secured at a position along a length of the cannula sleeve.

In still yet another aspect, the cannula sleeve may include an inflatable balloon at a distal portion of the cannula sleeve. The inflatable balloon may be in communication with the inflation port of the cannula housing.

In still yet another aspect, the suction cup may have a lip extending radially inwards from a peripheral portion of the suction cup to establish a planar contact with tissue in a sealing relation.

BRIEF DESCRIPTION OF DRAWINGS

A cannula assembly is disclosed herein with reference to the drawings, wherein.

DETAILED DESCRIPTION

A cannula assembly is described in detail with reference to the drawings, wherein like reference numerals designate corresponding elements in each of the several views. As used herein, the term "distal" refers to that portion of the instrument, or component thereof which is farther from the user while the term "proximal" refers to that portion of the instrument or component thereof which is closer to the user. In addition, the terms parallel and perpendicular are understood to include relative configurations that are substantially parallel and substantially perpendicular up to about + or −10 degrees from true parallel and true perpendicular. Further, to the extent consistent, any or all of the aspects detailed herein may be used in conjunction with any or all of the other aspects detailed herein.

Figure 1:
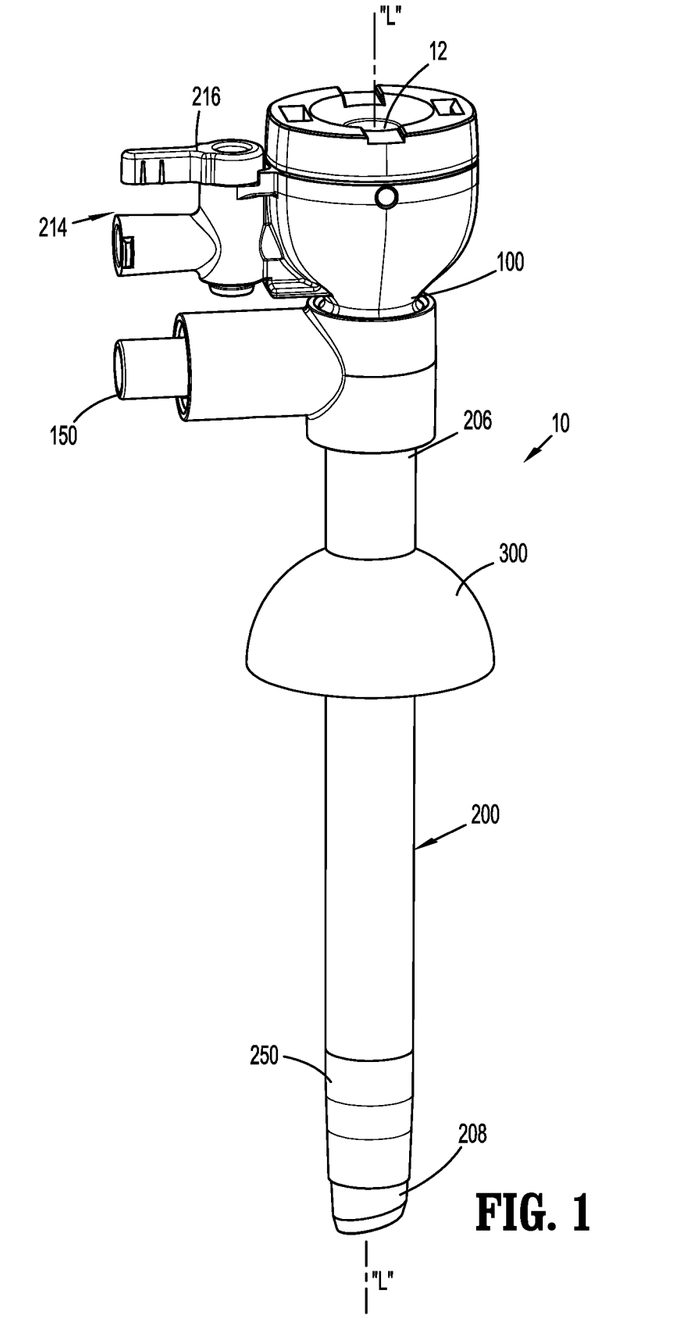
FIG. 1 is a perspective view of a cannula assembly including a suction cup in accordance with the disclosure.
Figure 2:
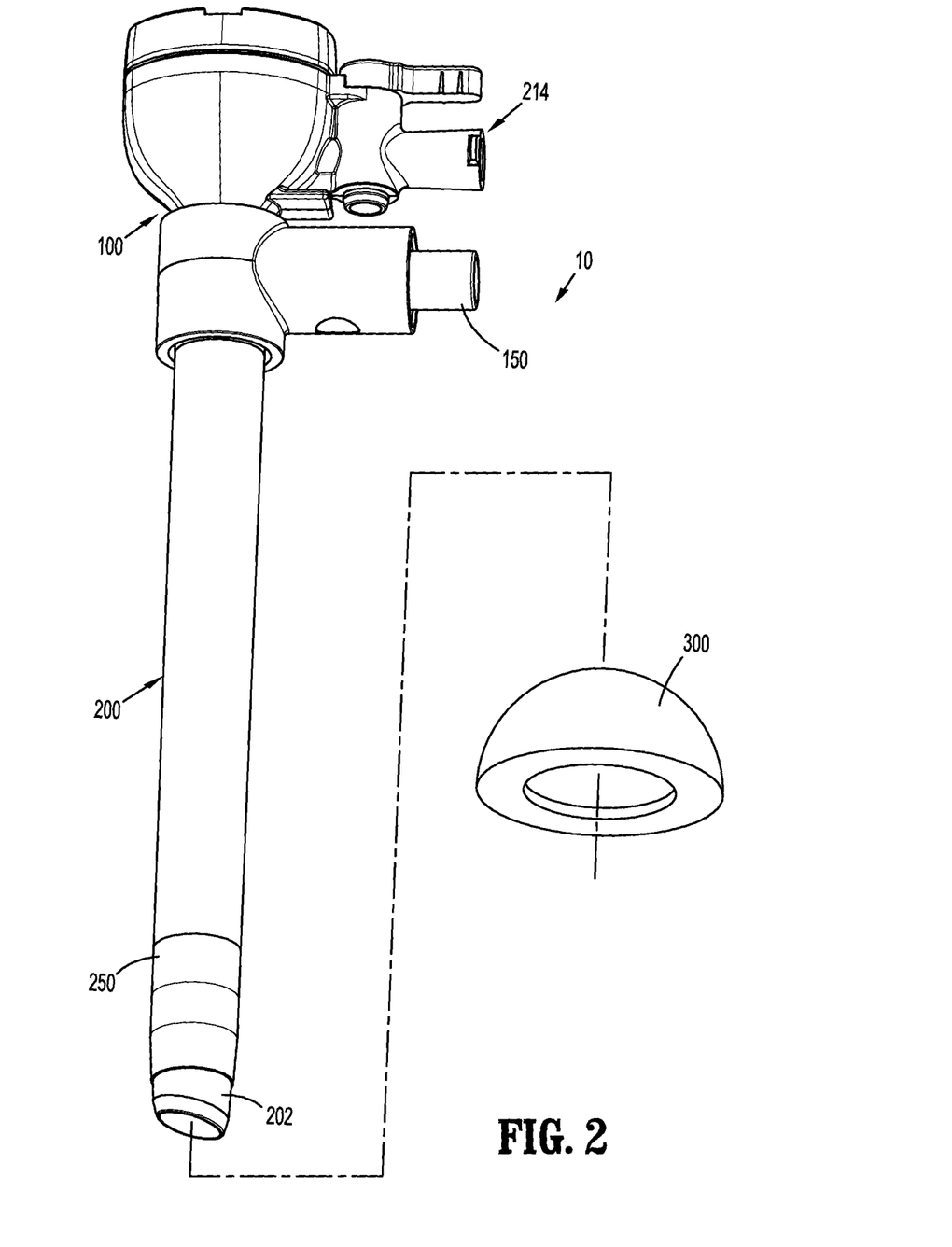
FIG. 2 is a perspective view of the cannula assembly of FIG. 1 with the suction cup separated from a cannula sleeve of the cannula assembly.

FIGS. 1 and 2 illustrate a cannula assembly in accordance with the disclosure shown generally as a cannula assembly 10. The cannula assembly 10 is configured to permit access to a surgical site such as, e.g., an insufflated abdominal cavity, during a laparoscopic procedure to permit the introduction of a surgical object for performing various surgical tasks on internal organs within the cavity. The surgical object may be a surgical instrument such as laparoscopic or endoscopic clip appliers, obturators, graspers, dissectors, retractors, staplers, laser probes, photographic devices, tubes, endoscopes and laparoscopes, electro-surgical devices, and the like. The cannula assembly 10 generally includes a cannula housing 100, a cannula sleeve 200 extending from the cannula housing 100, and a suction cup 300 adjustably disposed on the cannula sleeve 200 to form a seal against tissue, as will be discussed.

The cannula housing 100 is configured for engagement by the clinician. The cannula sleeve 200 includes proximal and distal end portions 206, 208 and defines a longitudinal axis "L-L" extending along the length of the cannula sleeve 200. The cannula housing 100 and the cannula sleeve 200 define a lumen 12 for reception and passage of a surgical object therethrough. The cannula housing 100 includes an insufflation port 214 and associated insufflation valve 216 (e.g., a stop cock valve) for selective introduction of insufflation fluids into the cannula sleeve 200 and the abdominal cavity. The lumen 12 is in fluid communication with the insufflation port 214 to convey the insufflation fluids into the abdominal cavity to establish and/or maintain the pneumoperitoneum.

The cannula housing 100 defines a cavity configured to adjustably support a seal assembly therein. The seal assembly may be supported within the cannula housing 100 to provide sealed passage of the surgical instrument through the cannula assembly 100. The cannula housing 100 may include a zero-closure valve, e.g., a duckbill valve, which is configured to close in the absence of a surgical object to prevent egress of insufflation gases.

The cannula assembly 10 may be configured for use with an obturator inserted through the lumen 12 of the cannula housing 100 and the cannula sleeve 200. The obturator may have a blunt distal end, or a bladed or non-bladed penetrating distal end. The obturator may be used to incise the abdominal wall so that the cannula assembly 10 may be introduced into the abdomen. A handle of the obturator may engage or selectively lock into the cannula housing 100 of the cannula assembly 10.

FIGS. 1 and 2 further illustrate the cannula sleeve 200 including a balloon anchor or an expandable member 250 at a distal end portion 202 of the cannula sleeve 200. The balloon anchor 250 is disposed about the cannula sleeve 200. The balloon anchor 250 is provided to secure cannula assembly 10 against body tissue, e.g., an inner surface of an abdominal wall. The cannula housing 100 includes an inflation port 150 which is in fluid communication with the balloon anchor 250. The inflation port 150 may be connected to a fluid supply to inflate the balloon anchor 250. It is contemplated that the cannula sleeve 200 may be without the balloon anchor 250. For example, the cannula sleeve 200 may include a ribbed surface to facilitate securement of the cannula sleeve 200 with tissue. Alternatively, the cannula sleeve 200 may include a smooth surface.

Figure 3:
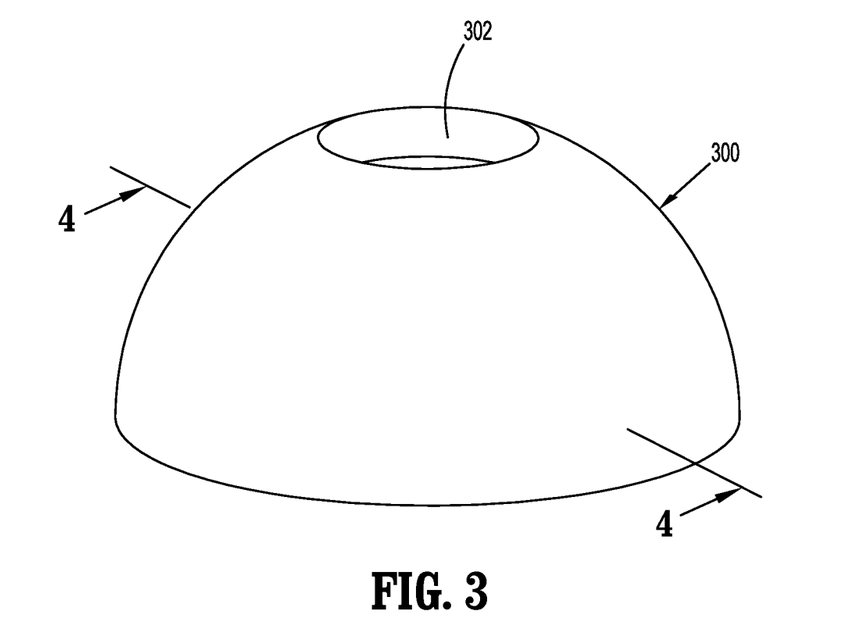
FIG. 3 is a perspective view of the suction cup of FIG. 1.
Figure 4:
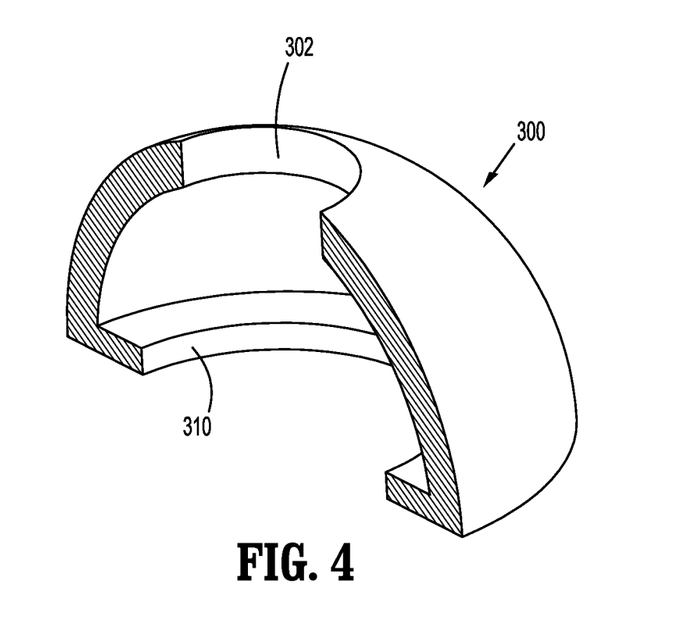
FIG. 4 is a perspective view of the suction cup of FIG. 3 taken along section line 4-4 of FIG. 3.

FIGS. 1 and 2 further illustrate the suction cup 300 adjustably disposed on the cannula sleeve 200. The suction cup 300 is provided to seal around an incision in the patient's abdominal wall and stabilize the cannula assembly 10 relative to the abdominal wall in conjunction with the balloon anchor 250. The suction cup 300 is formed of a compressible material. The suction cup 300 is formed of a flexible material that creates suction when pressed against tissue and forms a seal about the incision in the abdominal wall. In particular, the suction cup 300 has a hemispherical shape defining a bore 302 (FIG. 3) dimensioned to receive the cannula sleeve 200 therethrough. The suction cup 300 includes a lip 310 (FIG. 4) extending radially inwards to engage tissue. Further, the lip 310 includes a planar surface to engage tissue in a sealing relation. For example, the suction cup 300 may be formed of the thermoplastic elastomer (TPE) commercially available under the tradename SANTOPRENE® from Advanced Elastomer Systems, L.P.

Figure 5:
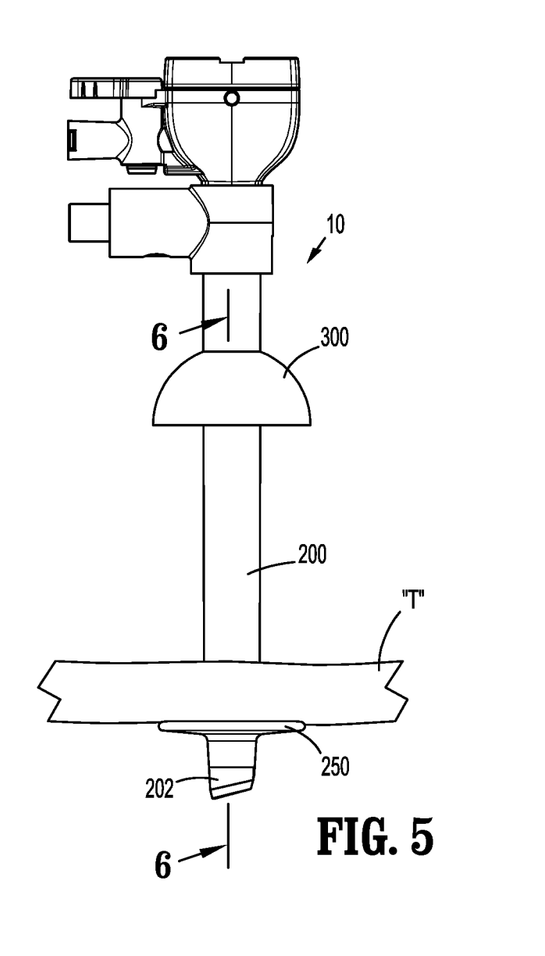
FIG. 5 is a side view of the cannula assembly of FIG. 1, illustrating the suction cup disposed on a cannula sleeve of the cannula assembly.
Figure 6:
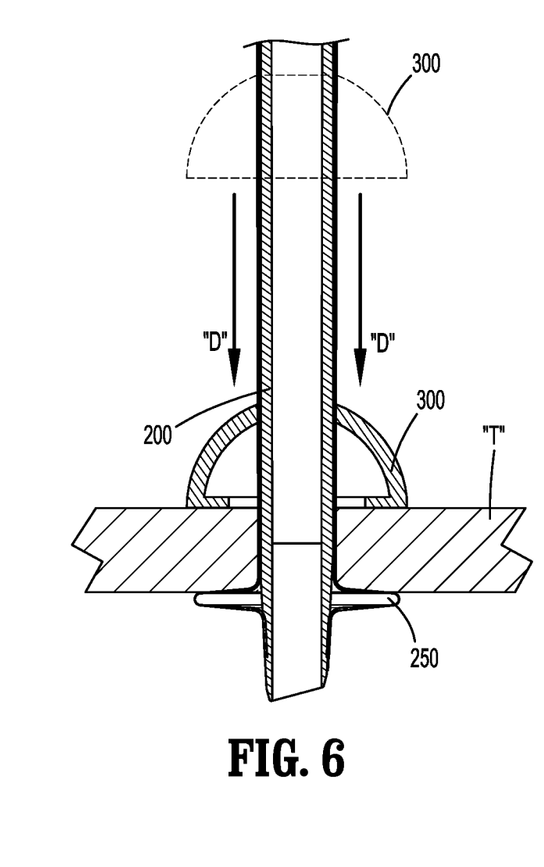
FIG. 6 is a side cross-sectional view of the cannula assembly of FIG. 5 taken along section line 6-6 of FIG. 5, illustrating displacement of the suction cup towards tissue.

FIGS. 5 and 6 illustrate the suction cup 300 frictionally supported on the cannula sleeve 200. Once the distal end portion 202 of the cannula sleeve 200 is inserted through an opening or an incision, the balloon anchor 250 may be inflated to secure the cannula assembly 10 to tissue "T" and to provide a seal against the opening or incision. At this time, the clinician may slide the suction cup 300 towards the balloon anchor 250, i.e., in the direction of arrows "D" such that the opening or the incision is closed by the balloon anchor 250 and the suction cup 300.

Figure 7:
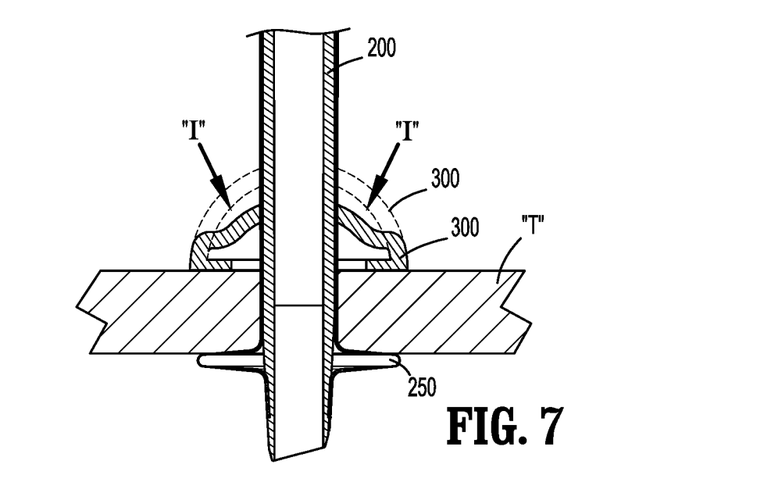
FIG. 7 is a side cross-sectional view of the cannula assembly of FIG. 6, illustrating compression of the suction cup to provide a fluid-tight seal against tissue.
Figure 8:
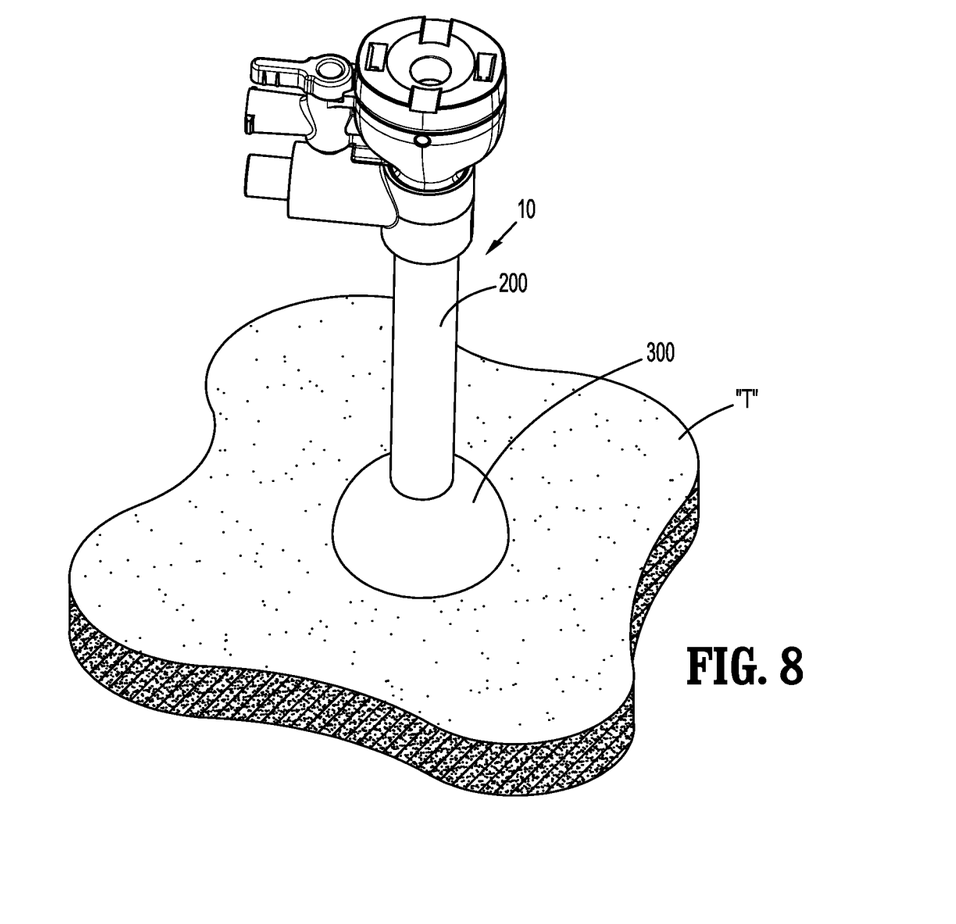
FIG. 8 is a perspective view of the cannula assembly of FIG. 1, illustrating securement of the cannula assembly with an opening in tissue.

FIGS. 7 and 8 illustrate the suction cup 300 forming a seal against tissue "T". The clinician presses the suction cup 300 towards the balloon anchor 250 in the direction of arrows "T". In this manner, the suction cup 300 is compressed and creates suction against tissue "T" such that the suction cup 300 seals around the opening or incision in tissue "T" and facilitates securement of the cannula assembly 10 in the opening or incision in tissue "T". Under such a configuration, the suction cup 300 and balloon anchor 250 enable off-axis movement of the cannula sleeve 200 while maintaining the pneumoperitoneum.

Figure 9:
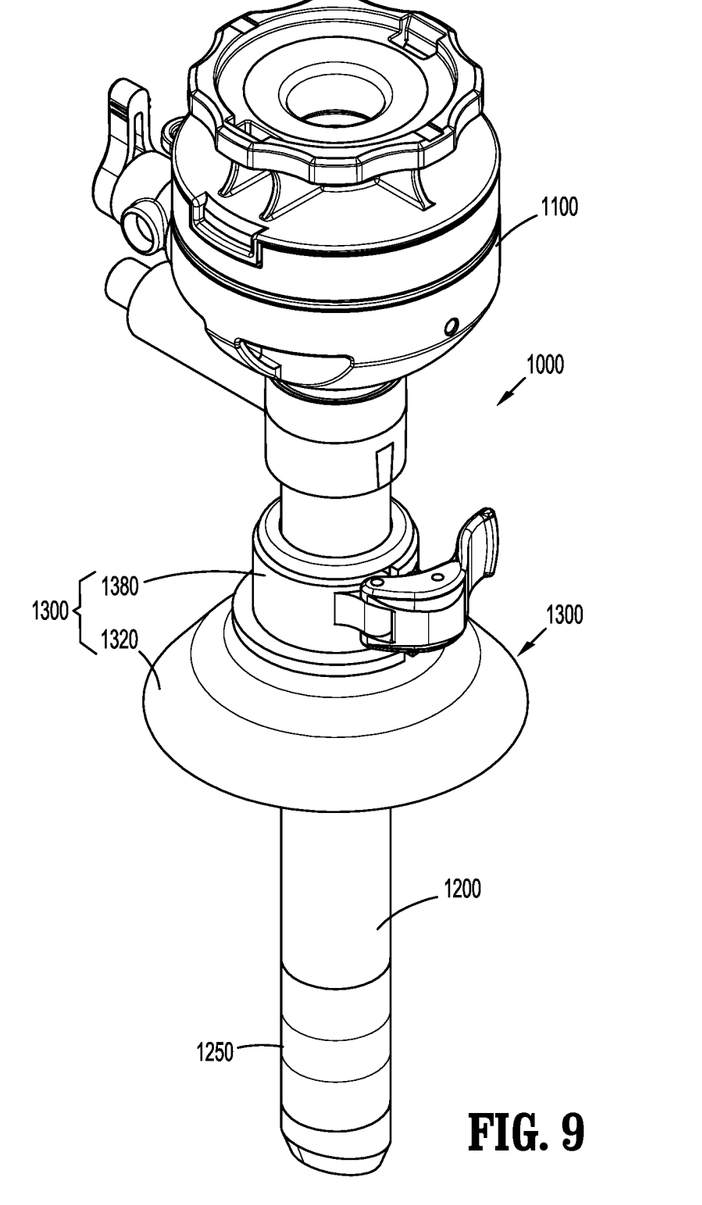
FIG. 9 is a perspective view of a cannula assembly including a suction cup assembly in accordance with another aspect of the disclosure.

FIG. 9 illustrates a cannula assembly 1000 including a suction cup assembly 1300 in accordance with another aspect of the disclosure. Parts of the cannula assembly 1000 substantially identical to the parts of the cannula assembly 10 (FIG. 1) will only be described herein to the extent necessary to identify differences in construction and/or operation. The suction cup assembly 1300 is formed of a flexible material that creates suction when pressed against tissue and forms a seal about the incision in the abdominal wall. The suction cup assembly 1300 includes a sealing component 1320 and a locking component 1380. The sealing component 1320 and the locking component 1380 may be detachably coupled to each other. The sealing component 1320 may be formed as a single construct. The suction cup assembly 1300 is adjustably securable at a position along a length of a cannula sleeve 1200.

Figure 10:
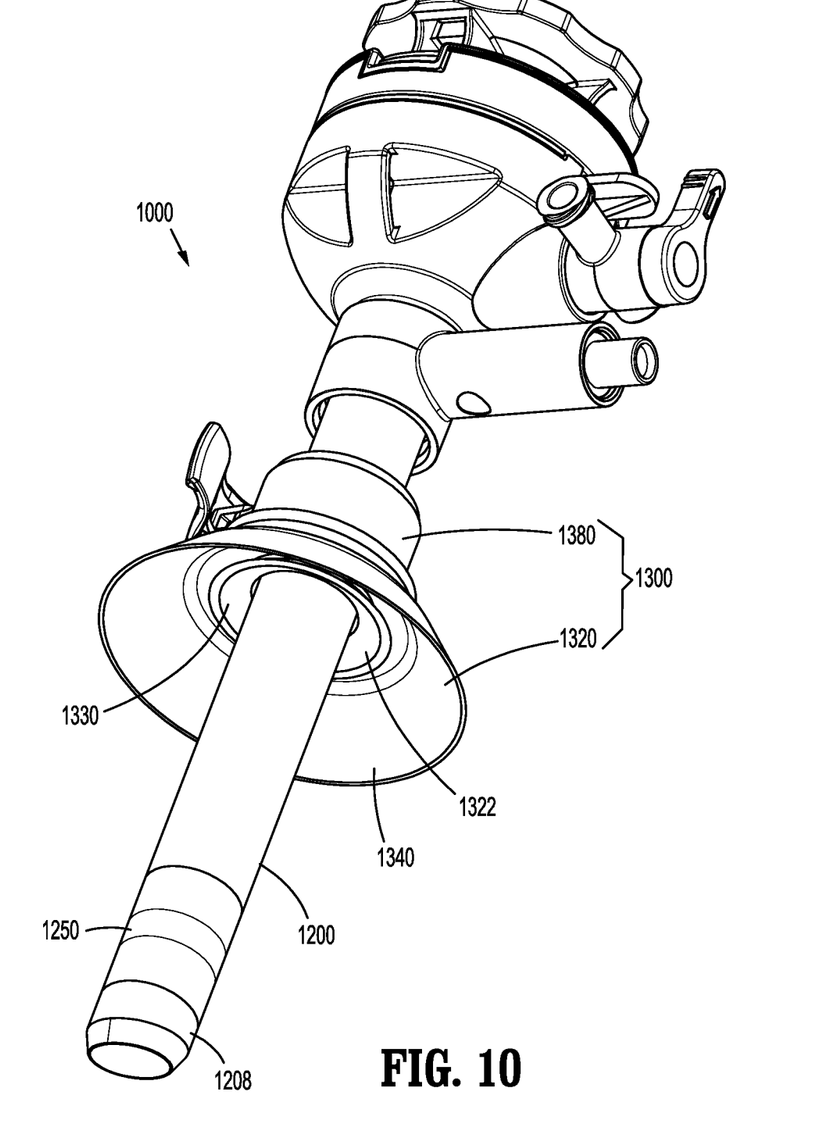
FIG. 10 is a bottom perspective view of the cannula assembly of FIG. 9.
Figure 11:
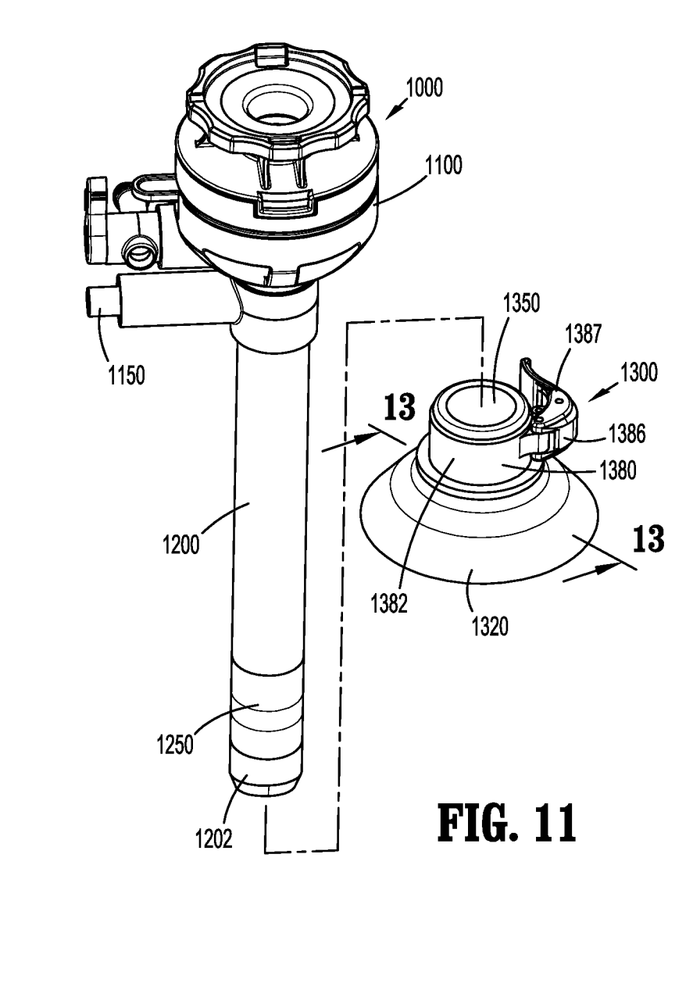
FIG. 11 is a perspective view of the cannula assembly of FIG. 10 with the suction cup assembly separated from a cannula sleeve of the cannula assembly.
Figure 12:
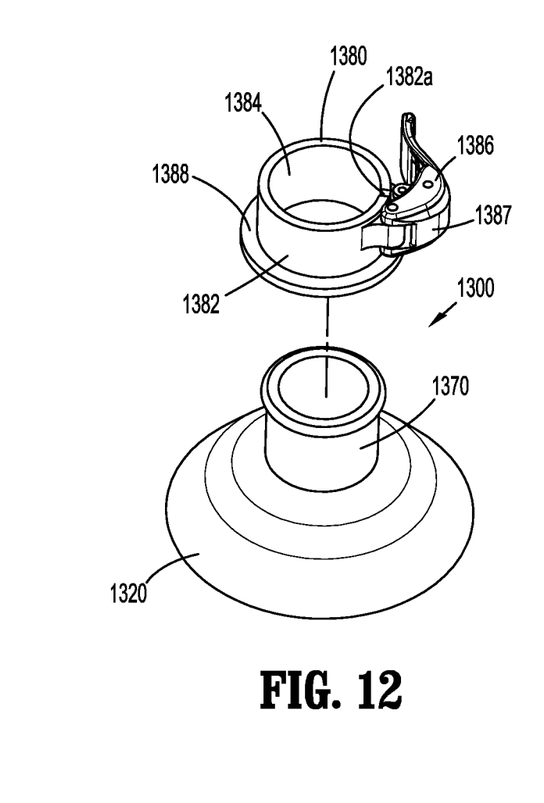
FIG. 12 is a perspective view of a suction cup assembly with parts separated.

FIGS. 10-12 illustrate the suction cup assembly 1300 that is adjustably securable on the cannula sleeve 1200. In particular, the sealing component 1320 of the suction cup assembly 1300 includes an inner cup 1330, an outer cup 1340, and a neck portion 1370 configured to support the locking component 1380. The inner and outer cups 1330, 1340 extend distally from the neck portion 1370. The inner cup 1330 is nested within the outer cup 1340. At least the inner cup 1330 and the outer cup 1340 are formed a compressible material such as, e.g., the thermoplastic elastomer (TPE) commercially available under the tradename SANTOPRENE® from Advanced Elastomer Systems, L.P. The sealing component 1320 may be monolithically formed. However, it is contemplated that the inner and outer cups 1330, 1340 may be formed of different materials to provide different compressibilities. Alternatively, the inner and outer cups 1330, 1340 may be formed of the same material, but have different thicknesses to provide different compressibilities. For example, the outer cup 1340 may be more compressible than the inner cup 1330 or vice versa.

Figures 13, 14:
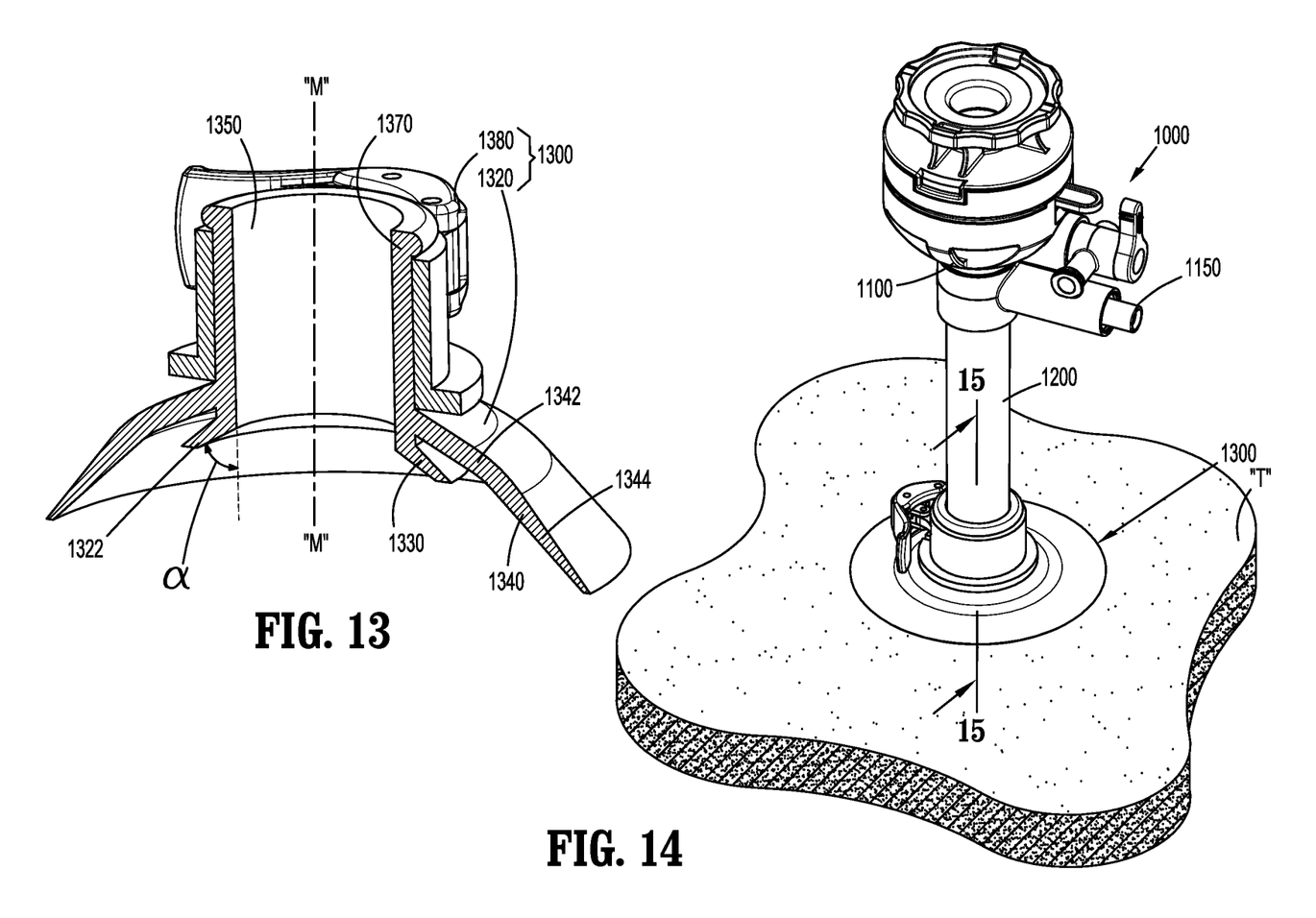
FIG. 13 is a partial perspective view of the suction cup assembly of FIG. 11 taken along section line 13-13 of FIG. 11.
FIG. 14 is a perspective view of the cannula assembly of FIG. 10, illustrating use thereof in a body cavity.

FIG. 13 illustrates the suction cup assembly 1300 defining a bore 1350 to receive the cannula sleeve 1200 (FIG. 1) in a sealing relation. The bore 1350 defines a longitudinal axis "M-M." The inner and outer cups 1330, 1340 may define an arcuate profile. The outer cup 1340 is disposed about the inner cup 1330. The inner cup 1330 includes an engaging portion 1322 configured to engage tissue in a sealing relation. The engaging portion 1322 defines an acute angle α with respect to the longitudinal axis "M-M" when the inner cup 1330 is uncompressed. However, when the inner cup 1330 is compressed, the engaging portion 1322 is configured to provide, e.g., a planar contact with tissue, to form a fluid-tight seal against tissue. The outer cup 1340 is disposed about the inner cup 1330 and extends radially outwards from the neck portion 1370. In particular, the outer cup 1340 includes a first portion 1342 that extends radially outwards from the neck portion 1370 and a second portion 1344 that deflects distally from the first portion 1342. At least the second portion 1344 may be distal of the inner cup 1330. Further, at least the second portion 1344 may be radially outwards of the inner cup 1330.

FIGS. 11 and 12 further illustrate the locking component 1380 of the suction cup assembly 1300. The locking component 1380 includes a locking sleeve 1382 defining a bore 1384 dimensioned to receive the neck portion 1370 of the sealing component 1320. A flange 1388 is coupled to a distal portion of the locking sleeve 1382 and extends radially from the distal portion of the locking sleeve 1382. The locking sleeve 1382 defines a slit 1382a. The locking mechanism 1386 includes a latch 1387 coupled to the locking sleeve 1382 on opposing slides of the slit 1382a to compress the locking sleeve 1382 and the neck portion 1370 of the sealing component 1320 radially inwards and against the cannula sleeve 1200 to secure the suction cup assembly 1300 against an outer surface of an abdominal wall.

FIG. 11 illustrates the suction cup assembly 1300 separated from the cannula assembly 1000 prior to use. The latch 1387 of the locking mechanism 1386 may be opened to enlarge the diameter of the locking sleeve 1382. The suction cup assembly 1300 is then placed over the cannula sleeve 1200. Thereafter, and with additional reference to FIG. 15, the distal end portion 1202 of the cannula sleeve 1200 is inserted through an incision or an opening and into a body cavity "BC." At this time, the balloon anchor 1250 may be inflated with a fluid introduced through an inflation port 1150 of the cannula housing 1100 such that the balloon anchor 1250 secures the cannula assembly 1000 in a sealing relation against tissue "T". At this time, the clinician may slide the suction cup assembly 1300 towards the balloon anchor 1250 such that tissue "T" is clamped between the balloon anchor 1250 and the suction cup assembly 1300, thereby the sealing component 1320 engages tissue "T" in a sealing relation. In particular, the inner cup 1330 makes, e.g., a planar contact, with tissue "T" to form a seal against tissue "T", and at least the second portion 1344 of the outer cup 1340 forms, e.g., a planar contact, with tissue "T" to form a seal against tissue "T" when the suction cup assembly 1300 is pressed against tissue "T". In this manner, the sealing component 1320 creates suction against tissue "T" and establishes a fluid-tight seal against tissue "T". At this time, the clinician may secure the suction cup assembly 1300 to the position by using the latch 1387 of the locking mechanism 1386. In this manner, the suction created by the compressed suction cup assembly 1300 maintains the seal against tissue "T", and thus pneumoperitoneum in the abdominal cavity.

Figure 15:
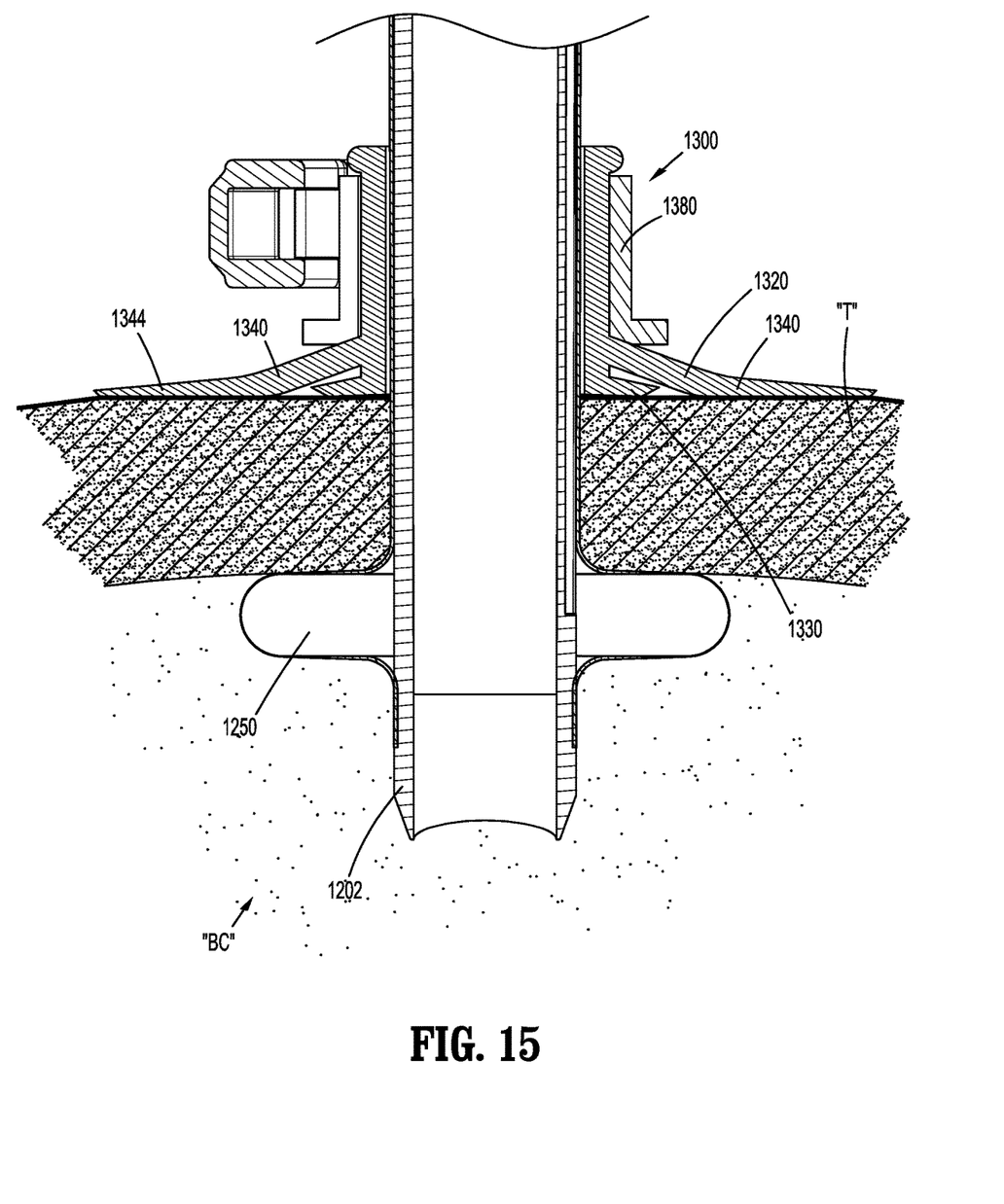
FIG. 15 is a side cross-sectional view of the cannula assembly of FIG. 14 taken along section line 15-15 of FIG. 14.

In use, initially, an incision is made in a body wall to gain entry to a body cavity, such as the abdominal cavity. The distal end portion 1208 of the cannula sleeve 1200 is inserted through the incision until at least the balloon anchor 1250 is within the body cavity. At this time, the balloon anchor 1250 is inflated. Thereafter, the suction cup assembly 1300 is moved distally such that tissue "T" is clamped between the balloon anchor 1250 and the suction cup assembly 1300. However, it is contemplated that the suction cup assembly 1300 may be utilized without the balloon anchor 1250. At this time, the clinician may compress the suction cup assembly 1300 against tissue "T" to create suction, thereby forming a fluid-tight seal against tissue "T". In order to maintain suction and the seal against tissue "T", the latch 1387 the locking mechanism 1386 is utilized to lock the position of the suction cup assembly 1300 relative to the cannula sleeve 1200. With the incision sealed, the body cavity may be insufflated with $CO_2$, a similar gas, or another insufflation fluid. Surgical instruments may be inserted through the cannula assembly 1000 to perform desired surgical procedures. The method of use of the cannula assembly 10 is substantially similar to the method of use of the cannula assembly 1000, and thus, will not be described herein.

It is further contemplated that the cannula assembly 10 may be used with an obturator. The obturator generally includes a head portion having latches configured to engage respective notches defined in the cannula housing 100 of the cannula assembly 10 to enhance securement therewith, an elongate shaft extending from the head portion, and an optical penetrating tip coupled to a distal end of the elongate shaft. The optical penetrating tip may be used to penetrate the skin and access the body cavity. By applying pressure against the proximal end of the obturator, the tip of the obturator is forced though the skin and the underlying tissue layers until the cannula and obturator enter the body cavity.

Persons skilled in the art will understand that the devices and methods specifically described herein and illustrated in the accompanying drawings are non-limiting. It is envisioned that the elements and features may be combined with the elements and features of another without departing from the scope of the disclosure. As well, one skilled in the art will appreciate further features and advantages of the disclosure.

What is claimed is:

1. A cannula assembly comprising:
   a cannula housing;
   a cannula sleeve extending distally from the cannula housing; and
   a suction cup assembly adjustably securable over the cannula sleeve, the suction cup assembly including:
     a sealing component including:
       a neck portion having an outer surface and opposing ends defining a bore that is coaxially alignable with the cannula sleeve, the bore defining a longitudinal axis; and
       an inner cup extending from the outer surface of the neck portion radially outward from the longitudinal axis, the inner cup defining an acute angle with respect to the longitudinal axis with the cannula sleeve extending through the bore of the neck portion;
       an outer cup extending from the outer surface of the neck portion radially outward from the longitudinal axis, wherein the outer cup of the sealing component includes a first portion extending from the neck portion and a second portion deflected distally from the first portion, wherein the second portion of the outer cup is distal of the inner cup, wherein the inner cup is spaced from the outer cup along the longitudinal axis thereby defining a gap between the inner cup and the outer cup, wherein the inner cup is nested within the outer cup, and wherein the sealing component is formed of a compressible material to create suction when pressed against tissue to form fluid-tight seals against tissue; and
     a locking component disposed about the neck portion of the sealing component, the locking component including a locking sleeve and a latch coupled to the locking sleeve to selectively compress the locking sleeve to adjustably secure the suction cup assembly at a position along the cannula sleeve.

2. The cannula assembly according to claim 1, wherein the cannula sleeve has an inflatable balloon disposed at a distal end portion of the cannula sleeve.

3. The cannula assembly according to claim 2, wherein the cannula housing includes an inflation port in communication with the inflatable balloon.

4. The cannula assembly according to claim 2, wherein the inner cup includes an engaging portion defining the acute angle with respect to the longitudinal axis when the inner cup is in an uncompressed state.

5. The cannula assembly according to claim 4, wherein the engaging portion of the inner cup includes a planar surface configured for planar contact with tissue in a sealing relation when the inner cup is compressed against tissue.

6. The cannula assembly according to claim 1, wherein the second portion of the outer cup includes a planar surface configured to be in planar contact with tissue when compressed against tissue in a sealing relation.

7. The cannula assembly according to claim 1, wherein at least the inner cup or the outer cup is formed of a thermoplastic elastomer.

8. The cannula assembly according to claim 1, wherein the sealing component of the suction cup assembly is monolithically formed.

9. The cannula assembly according to claim 1, wherein the locking sleeve defines a slit to enable enlarging of the diameter of the locking sleeve by the latch.

10. The cannula assembly according to claim 1, wherein the second portion of the outer cup is disposed radially outwards of the inner cup when the suction cup assembly is compressed against tissue.

11. The cannula assembly according to claim 1, wherein the locking sleeve has a flange at a distal portion of the locking sleeve, the flange configured to engage the outer cup of the sealing component to urge the outer cup radially outwards when the suction cup assembly is compressed against tissue.

12. A cannula assembly comprising:
    a cannula housing including an inflation port;
    a cannula sleeve extending from the cannula housing, the cannula housing and the cannula sleeve defining a lumen configured to receive a surgical instrument;
    a neck having an outer surface, a first end, and a second end defining a bore that is coaxially alignable with the cannula sleeve, the bore defining a longitudinal axis; and
    a suction cup extending from the neck and adjustably disposed over the cannula sleeve, the suction cup having an inner cup and an outer cup defining a dome shape, the inner cup extending from the outer surface of the neck radially outward from the longitudinal axis and the outer cup extending from the outer surface of the neck radially outward from the longitudinal axis at a position that is axially spaced from the inner cup along the longitudinal axis,
    wherein the outer cup includes a first portion extending from the neck and a second portion deflected distally from the first portion, wherein the second portion of the outer cup is distal of the inner cup, wherein the inner cup defines an acute angle with respect to the longitudinal axis with the cannula sleeve extending through the bore of the neck, and wherein the suction cup is compressible to form suction, thereby forming a seal against tissue.

13. The cannula assembly according to claim 12, wherein the suction cup is formed of a thermoplastic elastomer.

14. The cannula assembly according to claim 12, wherein the suction cup defines a proximal aperture dimensioned to receive the cannula sleeve in a sealing relation.

15. The cannula assembly according to claim 14, wherein the suction cup further defines a distal aperture having a diameter larger than a diameter of the proximal aperture.

16. The cannula assembly according to claim 12, wherein the suction cup is frictionally secured at a position along a length of the cannula sleeve.

17. The cannula assembly according to claim 12, the cannula sleeve includes an inflatable balloon at a distal portion of the cannula sleeve, the inflatable balloon in communication with the inflation port of the cannula housing.

18. The cannula assembly according to claim 12, wherein the suction cup has a lip extending radially inwards from a peripheral portion of the suction cup and is configured to establish a planar contact with tissue in a sealing relation.

* * * * *